(12) United States Patent
Vanearden (10) Patent No.: US 7,380,615 B1
(45) Date of Patent: Jun. 3, 2008

(54) CORE SAMPLE EXTRACTION SYSTEM

(76) Inventor: David L. Vanearden, 9394 Brownell Rd., Clymer, NY (US) 14724

( * ) Notice: Subject to any disclaimer, the term of this patent is extended or adjusted under 35 U.S.C. 154(b) by 1 day.

(21) Appl. No.: 11/467,742

(22) Filed: Aug. 28, 2006

(51) Int. Cl.
*E21B 49/02* (2006.01)

(52) U.S. Cl. ............... 175/20; 73/864.31; 73/864.44; 73/864.91; 111/92; 175/58

(58) Field of Classification Search ............... 175/20, 175/58; 47/48.1; 111/92; 73/864.31, 864.44, 73/864.91
See application file for complete search history.

(56) References Cited

U.S. PATENT DOCUMENTS

| | | | | |
|---|---|---|---|---|
| 3,163,241 A | * | 12/1964 | Daigle et al. | 175/237 |
| 3,326,049 A | * | 6/1967 | Eley | 73/429 |
| 3,444,938 A | * | 5/1969 | Ballmann | 111/101 |
| 3,696,873 A | | 10/1972 | Anderson | |
| 3,786,877 A | | 1/1974 | Schafer et al. | |
| 4,549,612 A | * | 10/1985 | Cushing | 175/20 |
| 4,790,392 A | | 12/1988 | Clements | |
| 4,989,678 A | * | 2/1991 | Thompson | 175/20 |
| 5,245,878 A | * | 9/1993 | Underwood | 73/864.44 |
| 5,343,771 A | * | 9/1994 | Turriff et al. | 73/864.44 |
| 5,921,328 A | | 7/1999 | Babineau et al. | |
| D433,292 S | | 11/2000 | Giannoni | |
| 6,712,161 B1 | * | 3/2004 | Dai | 175/58 |

\* cited by examiner

*Primary Examiner*—William P Neuder (57) ABSTRACT

A core sample extraction system for extracting a plug from soil and removing the plug from the device so that the soil and any roots in the plug can be analyzed includes a boring tube including a top end and a bottom end. The bottom end is driven into soil to isolate a plug of the soil when the boring tube is struck by a mallet. An extraction assembly is positioned in the boring tube. The extraction assembly engages the plug in the boring tube and pushes the plug out of the bottom end when the extraction assembly is forced through the boring tube.

13 Claims, 7 Drawing Sheets

CORE SAMPLE EXTRACTION SYSTEM

BACKGROUND OF THE INVENTION

1. Field of the Invention

The present invention relates to soil sampling devices and more particularly pertains to a new soil sampling device for extracting a plug from soil and removing the plug from the device so that the soil and any roots in the plug can be analyzed.

2. Description of the Prior Art

The use of soil sampling devices is known in the prior art. U.S. The prior art commonly teaches the use of a sampler that retrieves a soil sample but does not provide a means for removing the soil sample from sampler. While these devices fulfill their respective, particular objectives and requirements, the need remains for a system that has certain improved features that provide for an extraction assembly to remove a plug of soil from the system once the plug has been retrieved by the system. Additionally, a support sleeve can be used to support the system over a bucket to allow the plug to be deposited into the bucket when the plug is extracted from the system.

SUMMARY OF THE INVENTION

The present invention meets the needs presented above by generally comprising a boring tube including a top end and a bottom end. The bottom end is driven into soil to isolate a plug of the soil when a mallet strikes the boring tube. An extraction assembly is positioned in the boring tube. The extraction assembly engages the plug in the boring tube and pushes the plug out of the bottom end when the extraction assembly is forced through the boring tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 10 thereof, a new soil sampling device embodying the principles and concepts of the present invention and generally designated by the reference numeral 10 will be described.

As best illustrated in FIGS. 1 through 10, the core sample extraction system 10 generally comprises a boring tube 12 including a top end 14 and a bottom end 16. The bottom end 16 is driven into soil to isolate a plug 1 of the soil when a mallet 2 strikes the boring tube 12. An extraction assembly 18 is positioned in the boring tube 12. The extraction assembly 18 engages the plug 1 in the boring tube 12 and pushes the plug 1 out of the bottom end 16 when the extraction assembly 18 is forced through the boring tube 12. A drive rod 20 extends into the boring tube 12 through the top end 14 of the boring tube 12. A protruding end 22 of the drive rod 20 is actuated to advance the drive rod 20 into the boring tube 12 and force the plug 1 out of the bottom end 16. A limiting collar 24 engages the drive rod 20. The limiting collar 24 is abutted against the top end 14 of the boring tube 12 to inhibit the drive rod 20 being fully driven into the boring tube 12.

In an embodiment, as shown in FIGS. 1 through 4, which is especially effective for loose soil, the extraction assembly 18 includes an extraction block 26 coupled to the drive rod 20 and positioned in the boring tube 12. The extraction block 26 is abutted against the plug 1 in the boring tube 12. The extraction block 26 abuts the plug 1 to force the plug 1 out of the boring tube 12. A stop fastener 28 is extended into the boring tube 12 between the extraction block 26 and the top end 14 of the boring tube 12. The extraction block 26 abuts against the stop fastener 28 to limit the depth the boring tube 12 is driven into the soil to retrieve the plug 1.

The boring tube 12 includes a strike plate 30 outwardly extending from the boring tube 12. The strike plate 30 is impacted by the mallet 2 to drive the bottom end 16 into the soil. The boring tube 12 includes a plurality of handles 32 outwardly extending from the boring tube 12. The handles 32 are graspable to facilitate removal of the boring tube 12 from the soil.

Figures 1, 2:
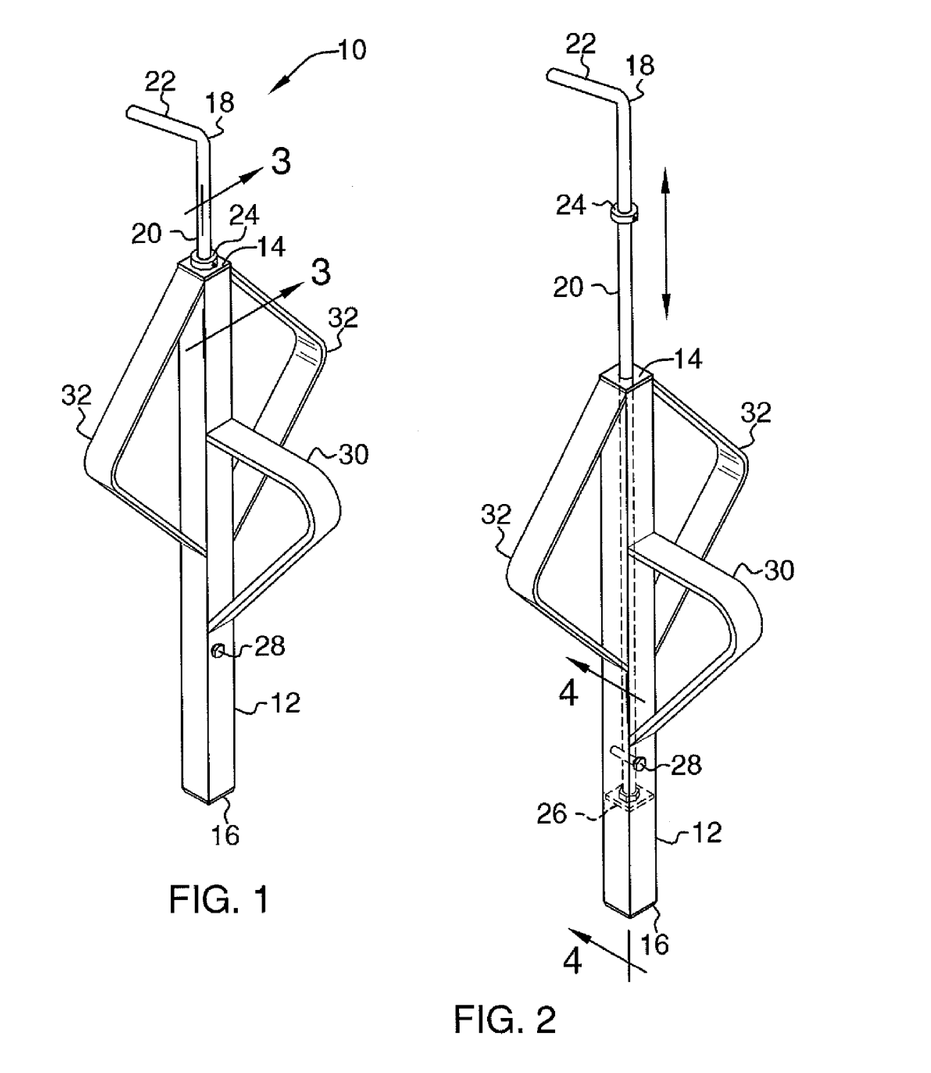
FIG. 1 is a perspective view of a core sample extraction system according to the present invention.
FIG. 2 is a perspective view of the present invention showing the extraction assembly being actuated.
Figures 3, 4:
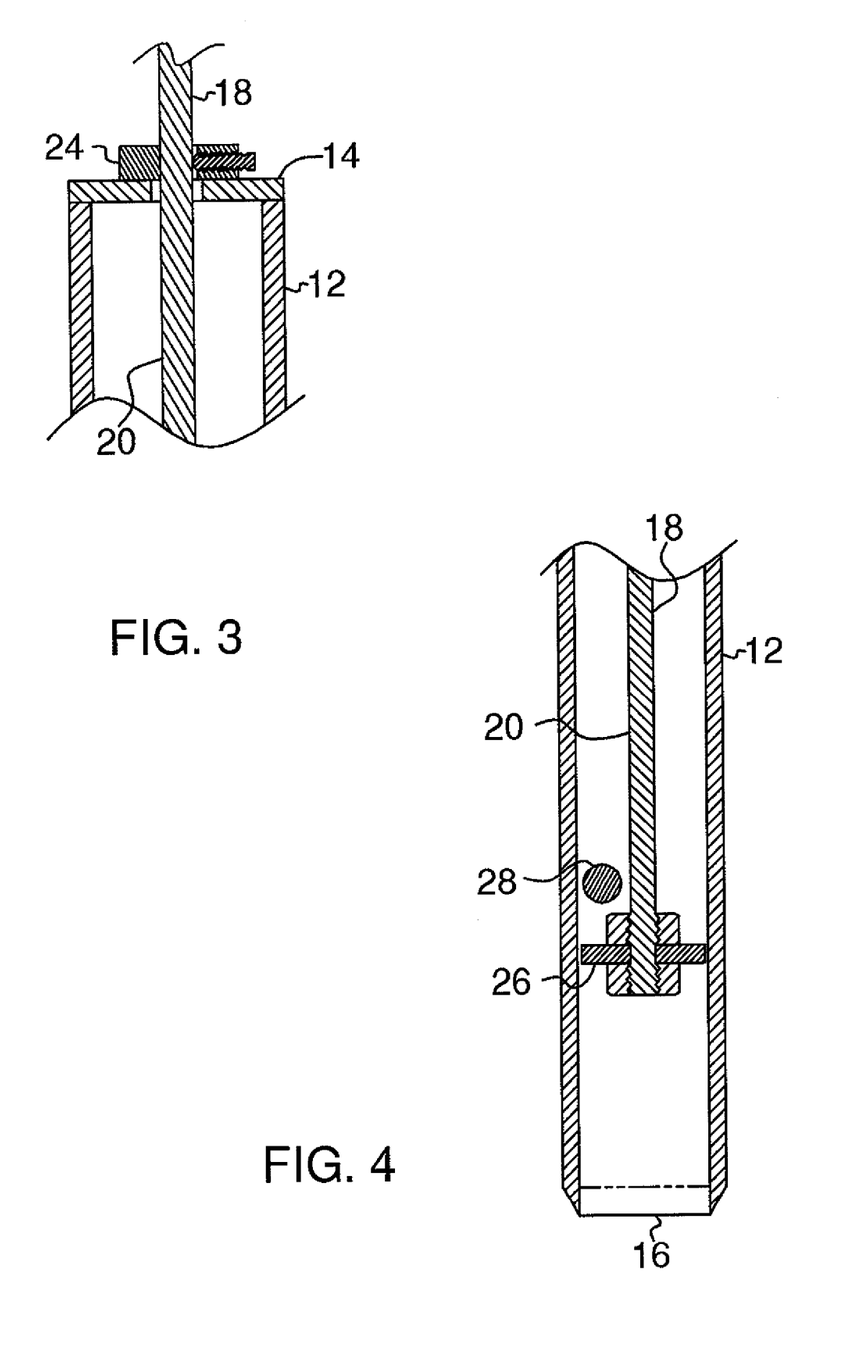
FIG. 3 is a cross-sectional view of the present invention taken along line 3-3 of FIG. 1.
FIG. 4 is a cross-sectional view of the present invention taken along line 4-4 of FIG. 2.
Figures 5, 6:
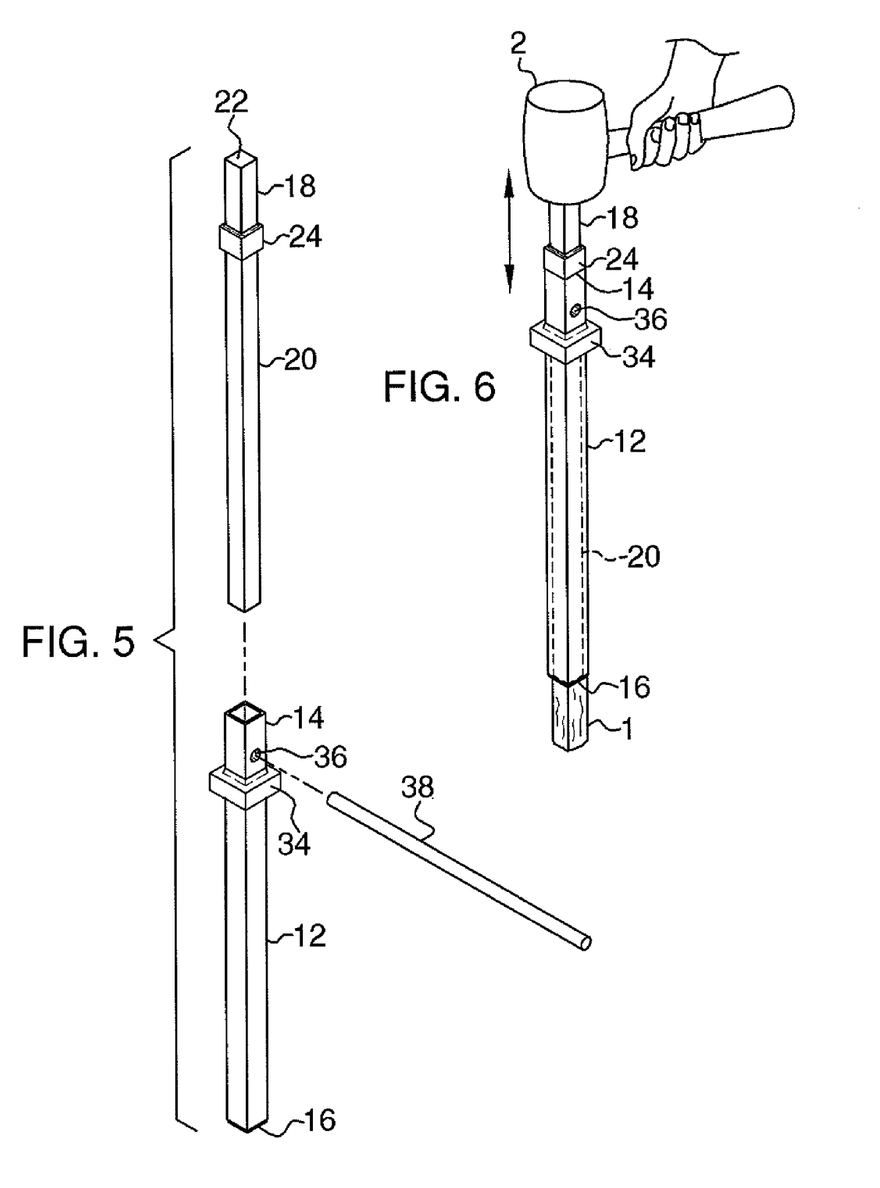
FIG. 5 is an exploded perspective view of an embodiment of the present invention.
FIG. 6 is a perspective view of the extraction assembly of the embodiment of the present invention shown in FIG. 5 being actuated.

In an embodiment, as shown in FIGS. 5 and 6, the boring tube 12 includes an abutting collar 34 outwardly extending from the boring tube 12 and being positioned adjacent the top end 14. The abutting collar 34 abuts the soil to indicate a maximum depth of the boring tube 12 is to be driven into the soil. The boring tube 12 has a receiving aperture 36 extending through the boring tube 12 orthogonal to a longitudinal axis of the boring tube 12. The receiving aperture 36 is positioned between the abutting collar 34 and the top end 14 of the boring tube 12. A retrieval bar 38 is slidably inserted into the receiving aperture 36 of the boring tube 12. The retrieval bar 38 is graspable on opposite sides of the boring tube 12 to remove the boring tube 12 and the plug 1 from the soil. The retrieval bar 38 is removed from the receiving aperture 36 when the extraction assembly 18 is to be positioned in the boring tube 12. The protruding end 22 of the drive rod 20 is struck to push the drive rod 20 towards the bottom end 16 and extract the plug 1.

Figure 7:
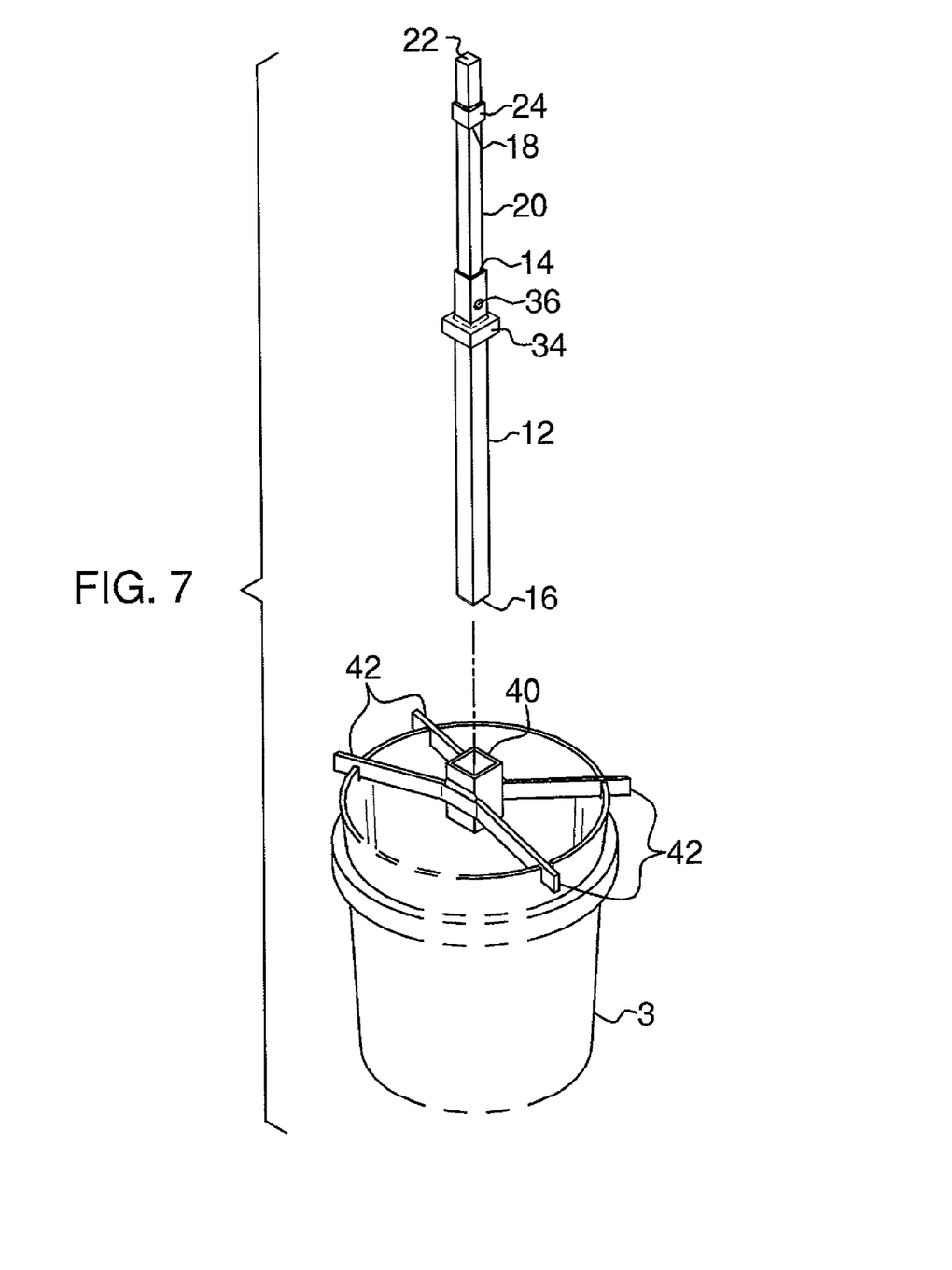
FIG. 7 is a perspective view of an embodiment of the present invention.
Figure 8:
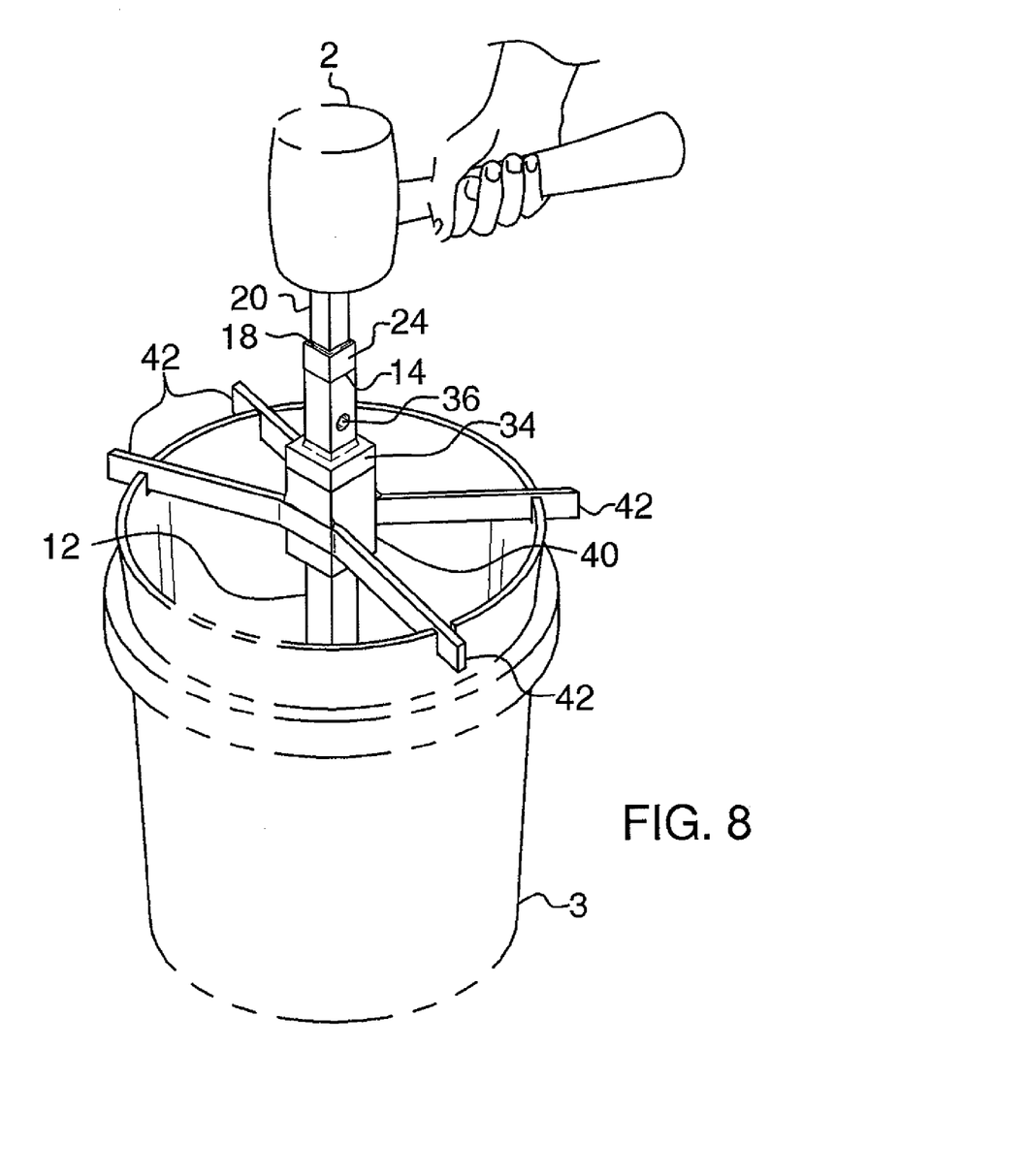
FIG. 8 is a perspective view of the extraction assembly of the embodiment of the present invention shown in FIG. 7 being actuated.

In an embodiment, as shown in FIGS. 7 and 8, a support sleeve 40 engages a bucket 3 to suspend the support sleeve 40 in the bucket 3. The bottom end 16 of the boring tube 12 is inserted into the support sleeve 40 and the boring tube 12 is slid through the support sleeve 40 and the abutting collar 34 rests on the support sleeve 40, wherein the boring tube 12 is suspended in the bucket 3. The support sleeve 40 includes a plurality of arms 42 outwardly extending from the support sleeve 40. Each of the arms 42 engages a rim of the bucket 3 to support the support sleeve 40 and the boring tube 12 in the bucket 3.

Figure 9:
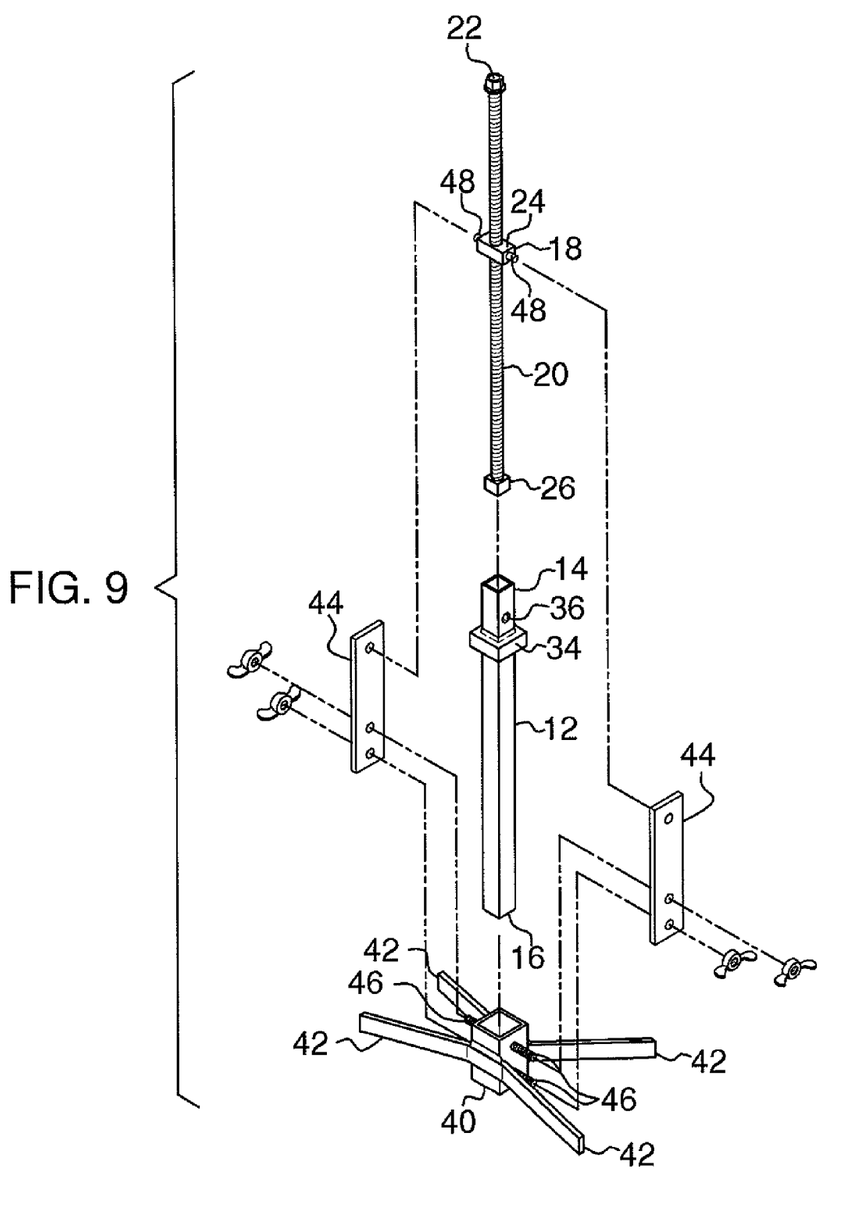
FIG. 9 is an exploded perspective view of an embodiment of the present invention.
Figure 10:
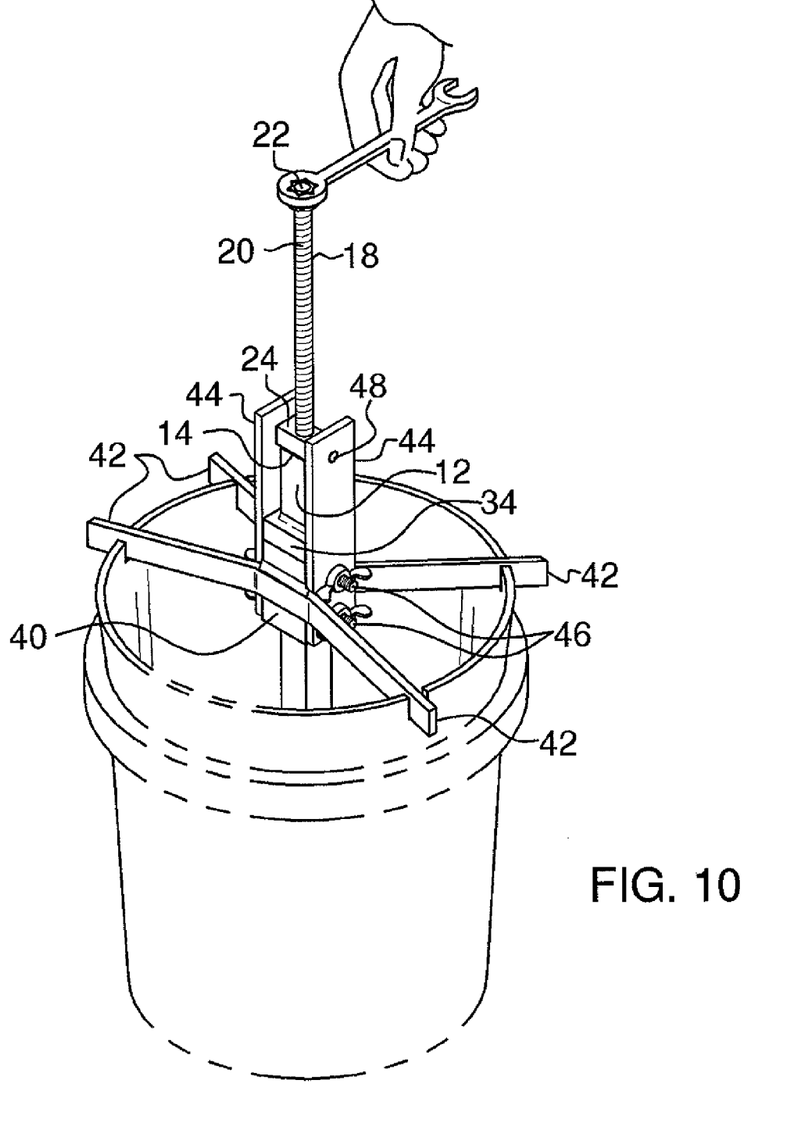
FIG. 10 is a perspective view of the extraction assembly of the embodiment of the present invention shown in FIG. 9 being actuated.

In an embodiment, as shown in FIGS. 9 and 10, the limiting collar 24 of the extraction assembly 18 threadably engages the drive rod 20. The protruding end 22 of the drive rod 20 is rotated to advance the drive rod 20 through the limiting collar 24 and slowly force the extraction block 26 towards the bottom end 16 to extract the plug 1 in a slow and controlled manner. Each of a pair of indexing plates 44 is secured to a pair of a plurality of securing pins 46 outwardly extending from the support sleeve 40. Each of the indexing plates 44 receives one of a pair of indexing pins 48 outwardly extending from the limiting collar 24 to inhibit rotation of the limiting collar 24 with respect to the boring tube 12 when the drive rod 20 is rotated.

In use, the bottom end 16 of the boring tube 12 is placed against the soil. The boring tube 12 is then struck by a mallet 2 to drive the bottom end 16 into the soil and isolate the plug 1 to be extracted. The boring tube 12 is twisted slightly to separate the plug 1 from the soil and then the boring tube 12 is removed from the soil. For loose soil, the protruding end 22 of the embodiment shown in FIGS. 1 through 4 is pushed toward the boring tube 12 to force the plug 1 out of the boring tube 12. For compacted soil, the embodiments shown in FIGS. 5 through 10 are used. The drive rod 20 is inserted into the top end 14 of the boring tube 12 and actuated appropriately to extract the plug 1 from the boring tube 12.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A core sample extraction system for obtaining a core sample of soil, said system comprising:
    a boring tube including a top end and a bottom end, said bottom end being driven into the soil to isolate a plug of the soil when said boring tube is struck by a mallet;
    an extraction assembly being positioned in said boring tube, said extraction assembly engaging the plug in said boring tube and pushing the plug out of said bottom end when said extraction assembly is forced through said boring tube, said extraction assembly including a drive rod extending into said boring tube through said top end of said boring tube, a protruding end of said drive rod being actuated to advance said drive rod into said boring tube and force the plug out of said bottom end, said extraction assembly including a limiting collar engaging said drive rod, said limiting collar being abutted against said top end of said boring tube to inhibit said drive rod being fully driven into said boring tube; and
    said boring tube including an abutting collar outwardly extending from said boring tube and being positioned adjacent said top end, said abutting collar abutting the soil to indicate a maximum depth of said boring tube is to be driven into the soil.

2. The system according to claim 1, wherein said extraction assembly includes an extraction block being coupled to said drive rod and positioned in said boring tube, said extraction block being abutted against the plug in said boring tube, said extraction block abutting the plug to force said plug out of said boring tube.

3. The system according to claim 2, further comprising a stop fastener being extended into said boring tube between said extraction block and said top end of said boring tube, said extraction block abutting against said stop fastener to limit the a size of the plug.

4. The system according to claim 2, wherein said boring tube includes a strike plate outwardly extending from said boring tube, said strike plate being impacted by the mallet to drive said bottom end into the soil.

5. The system according to claim 4, wherein said boring tube includes a plurality of handles outwardly extending from said boring tube, said handles being graspable to facilitate removal of said boring tube from the soil.

6. The system according to claim 1, wherein said boring tube has a receiving aperture extending through said boring tube orthogonal to a longitudinal axis of said boring tube, said receiving aperture being positioned between said abutting collar and said top end of said boring tube.

7. The system according to claim 6, further comprising a retrieval bar being slidably inserted into said receiving aperture of said boring tube, said retrieval bar being graspable on opposite sides of said boring tube to remove said boring tube and the plug from the soil, said retrieval bar being removed from said receiving aperture when said extraction assembly is to be positioned in said boring tube.

8. The system according to claim 7, further comprising a support sleeve engaging a bucket to suspend said support sleeve in the bucket, said bottom end of said boring tube being inserted into said support sleeve and said boring tube is slid through said support sleeve and said abutting collar rests on said support sleeve, wherein said boring tube is suspended in the bucket.

9. The system according to claim 8, wherein said support sleeve includes a plurality of arms outwardly extending from said support sleeve, each of said arms engaging a rim of the bucket to support said support sleeve and said boring tube in the bucket.

10. The system according to claim 8, wherein said limiting collar threadably engages said drive rod, said protruding end of said drive rod being rotated to advance said drive rod through said limiting collar and forcing the plug from said bottom end.

11. The system according to claim 10, wherein said extraction assembly includes an extraction block being coupled to said drive rod and positioned in said boring tube, said extraction block being abutted against the plug in said boring tube, said extraction block abutting the plug to force said plug out of said boring tube.

12. The system according to claim 10, further comprising a pair of indexing plates, each of said indexing plates being secured to a pair of a plurality of securing pins outwardly extending from said support sleeve, each of said indexing plates receiving one of a pair of indexing pins outwardly extending from said limiting collar to inhibit rotation of said limiting collar with respect to said boring tube when said drive rod is rotated.

13. A core sample extraction system for obtaining a core sample of soil, said system comprising:
  a boring tube including a top end and a bottom end, said bottom end being driven into the soil to isolate a plug of the soil when said boring tube is struck by a mallet, said boring tube including an abutting collar outwardly extending from said boring tube and being positioned adjacent said top end, said abutting collar abutting the soil to indicate a maximum depth of said boring tube is to be driven into the soil, said boring tube having a receiving aperture extending through said boring tube orthogonal to a longitudinal axis of said boring tube, said receiving aperture being positioned between said abutting collar and said top end of said boring tube;
  a retrieval bar being slidably inserted into said receiving aperture of said boring tube, said retrieval bar being graspable on opposite sides of said boring tube to remove said boring tube and the plug from the soil;
  an extraction assembly being positioned in said boring tube when said retrieval bar has been removed from said receiving aperture, said extraction assembly engaging the plug in said boring tube and pushing the plug out of said bottom end when said extraction assembly is forced through said boring tube, said extraction assembly comprising;
    a drive rod extending into said boring tube through said top end of said boring tube, a protruding end of said drive rod being actuated to advance said drive rod into said boring tube and force the plug out of said bottom end;
    a limiting collar engaging said drive rod, said limiting collar being abutted against said top end of said boring tube to inhibit said drive rod being fully driven into said boring tube, said limiting collar threadably engaging said drive rod, said protruding end of said drive rod being rotated to advance said drive rod through said limiting collar and forcing the plug from said bottom end;
    an extraction block being coupled to said drive rod and positioned in said boring tube, said extraction block being abutted against the plug in said boring tube, said extraction block abutting the plug to force said plug out of said boring tube;
  a support sleeve engaging a bucket to suspend said support sleeve in the bucket, said bottom end of said boring tube being inserted into said support sleeve and said boring tube is slid through said support sleeve and said abutting collar rests on said support sleeve, wherein said boring tube is suspended in the bucket, said support sleeve including a plurality of arms outwardly extending from said support sleeve, each of said arms engaging a rim of the bucket to support said support sleeve and said boring tube in the bucket; and
  a pair of indexing plates, each of said indexing plates being secured to a pair of a plurality of securing pins outwardly extending from said support sleeve, each of said indexing plates receiving one of a pair of indexing pins outwardly extending from said limiting collar to inhibit rotation of said limiting collar with respect to said boring tube when said drive rod is rotated.

* * * * *